United States Patent [19]

Pietsch et al.

[11] 4,169,121

[45] Sep. 25, 1979

[54] ABSORBENT MATERIAL FOR AQUEOUS PHYSIOLOGICAL FLUIDS AND PROCESS FOR ITS PRODUCTION

[76] Inventors: Helmut Pietsch, Danziger Platz 9, D-8500 Nüremburg; Walter Horn, Hellmuth-Hirth-Weg 2, D-8500 Nüremburg, both of Fed. Rep. of Germany

[21] Appl. No.: 831,755

[22] Filed: Sep. 9, 1977

[51] Int. Cl.$^2$ .................. C08L 1/24; D02G 3/02; A61F 13/20

[52] U.S. Cl. .................. 264/103; 106/165; 106/168; 128/285; 264/191

[58] Field of Search ........... 106/168, 165; 264/191, 264/103, 188; 128/284

[56] References Cited

U.S. PATENT DOCUMENTS

| | | | |
|---|---|---|---|
| 3,423,167 | 1/1969 | Kuzmak et al. | 264/191 |
| 3,843,378 | 10/1974 | Smith | 128/284 |

*Primary Examiner*—Theodore Morris
*Attorney, Agent, or Firm*—Isler and Ornstein

[57] ABSTRACT

An absorbent material is provided having exceptional fluid suction and holding power for aqueous physiological fluids, and which is thus especially adaptable for use as tampons, sanitary napkins, baby diapers, hospital pads and the like. The material consists essentially of cellulose fibers containing from 5 to 20% by weight of sodium carboxymethyl cellulose. The material is formed by a process in which a viscose spinning solution is produced from cellulose xantogenate by dissolving in aqueous caustic soda solution and permitting the solution to ripen, spinning the latter in an acid spinning bath, and then cleaning and drying the resultant threads, the spinning solution containing 5 to 20% by weight of sodium carboxymethyl cellulose.

3 Claims, No Drawings

ABSORBENT MATERIAL FOR AQUEOUS PHYSIOLOGICAL FLUIDS AND PROCESS FOR ITS PRODUCTION

The invention concerns an absorbent material with great fluid suction and holding power, for aqueous physiological fluids. Such absorbent materials are used in hygienic one-use articles, such as tampons for feminine hygiene, sanitary napkins, baby diapers, hospital pads and similar articles. They have the property of absorbing as quickly as possible, on wetting, the physiological fluids occurring, and holding them fast, even under the effect of pressure.

As absorbent material for these purposes, cellulose is still used today, as a rule, in the form of short or long fibers. The use of other materials for this purpose is also known, such as hydrophil polyurethane foams (Ger. Disclosure No. 1,198,060), for example, or suitable polymers, such as polyacrylamide or Poly-N-vinyl pyrrolidone and others (Ger. Disclosure No. 1,617,998). The use is also known, as aids to absorption, and thus as additives, of netted cellulose fibers, especially formalized that is, crosslinking with formaldehyde cotton or rayon fibers (Ger. Disclosure No. 1,492,365).

The use of the last-named materials, in addition to or instead of cellulose fibers is only reasonable, economically and technically, if these materials have a considerably heightened fluid absorption and holding power, as compared with pure cellulose. Any possible increase of these properties means technically a considerable gain, and makes the use of the said material possible, economically, for the first time, in many cases. But it is important, naturally, in all cases, that the said materials are fully unobjectionable physiologically, which, for example, is not the case with polyacrylates, according to recent research.

With this State of the Art, the problem exists of proposing an absorbent material for aqueous physiological fluids, which, compared with the known materials, with fuller physiological unobjectionability, has a considerably heightened suction power.

This problem is solved by the fact that, starting with an absorptive material based on partly netted (reticulated), especially formalized cellulose fibers, which is distinguished, according to the invention, by the fact that the partly netted, especially formalized cellulose fibers contain in their fibers 5-20% by weight, preferably 10% by weight, sodium carboxymethyl cellulose. The expression "in the fibers" is intended to mean that it is not a matter of a mixture of different fibers, but rather that the fiber is physically a unified structure, which only consists chemically of the said two materials, namely, regenerated cellulose, on the one hand, and sodium carboxymethyl cellulose in the said amount, on the other. It has been found that fibers so made up have an unexpected absorption value, and namely, both as to short-time values (suction values) and also long-term values (power to hold the fluid fast).

The fibers proposed, according to the invention, have, to advantage, a titer of 1.5 to 10.0, preferably 1.5 to 3.5 dtex, and a length of 20 to 120 mm, preferably 50 mm. It has proved favorable when the fibers are revived with polyethylene glycol of a molecular weight 200 to 20,000, preferably 400 to 4,000.

For the production of the proposed fibers, we start with the viscose process, known per se. Cellulose xanthogenate is processed by dissolving in aqueous caustic soda solution and allowing the solution to ripen to a viscous spinning solution. This spinning solution is then spun in an acid spinning bath and then the resultant threads are cleaned and dried. For production of the proposed fibers, there is added to the spinning solution 5 to 20% by weight, preferably 10% by weight, of sodium carboxymethyl cellulose, based on the cellulose contained in the solution, and the threads obtained in the spinning, after their cleaning in the manner known per se, in acid solution are partly netted (reticulated), especially formalized, and then the sodium salt is formed again by washing the fiber with sodium hydrogen carbonate solution, or similarly.

By this process it is possible to incorporate the said amounts of sodium carboxymethyl cellulose into the fiber and by the said partial reticulation, especially formalizing, to bind it with the rest of the cellulose molecules so that, in all, a chemically unified structure results, from which the sodium carboxymethyl cellulose molecule can no longer be removed by washing. There results in this way a fiber material with greatly increased suction values, these values being almost doubled as compared with most other physiologically unobjectionable absorbent materials to be considered. To demonstrate the advantageous properties of the absorbent material proposed, the examples of comparison listed below were carried out.

EXAMPLE 1

Production of the proposed absorbent material

We started with a mixed fiber of 90% cellulose and 10% sodium carboxymethyl cellulose. The fiber had a titer of 1.7 dtex and a section length of 50 mm.

For the formalizing, the following bath was prepared:
1125 ml water
1875 ml conc. hydrochloric acid (37%)
750 ml formaldehyde solution
3750 ml Into this bath were put, at a temperature of 20° C. 100 grams of the staple fiber described above. After 20 minutes stay time, the fiber was removed and washed neutral with water. Then the fiber was put into 2 liters of a 10% solution of sodium-hydrogen carbonate, to form back the sodium salt of the carboxymethyl cellulose. The action time was 10 minutes.

After reforming the salt form, the fibers were washed neutral again, the last wash water containing 0.5% polyethylene glycol of molecular weight 400. Then it was dried at 115° C.

EXAMPLE 2

Production of experimental tampons

The fiber prepared according to Example 1, was carded in the usual way, formed to strips 50 mm. wide and by winding and pressing, tampon bodies were produced.

In the same way, tampons were produced from various comparison fibers, in which the tampon raw weight in each case was about 3.0 grams. As comparison fibers, the following were used:
1. 100% cellulose, 3.6 dtex, 30 mm.
2. Non-formalized mixed fiber of cellulose and 10% carboxymethyl cellulose. This was the same fiber as that taken above as initial product for formalization. Titer: 1.7 dtex; 50 mm. fiber length.
3. Cellulose, Titer 5.2 dtex, 40 mm. staple length; formalized.

In all the experimental tampons, the expansion after 1 minute, after 3 minutes and after 15 minutes was measured against a pressure of 170 mm. water column, and the volume expansion, dependent on time, determined by collecting and weighing the amount of water driven out. The synthetic blood fluid had the following composition:

70 grams Tylose H 20 (Hoechst)
50 grams NaCl
20 grams $NaHCO_3$
5 grams red coloring
500 grams glycerine
Water to make up 5000 ml.

The values for fluid absorption after 15 minutes were determined by weighing back. The values obtained appear from the following table:

| Tampon | Weight | Expansion (ml) | | | Fluid absorption after 15 min (ml) |
|---|---|---|---|---|---|
| | | 1 min | 3 min | 15 min | |
| Cellulose, 100% 3,6 dtex/30 mm | 3,02 | 3,4 | 6,8 | 10,8 | 13,8 |
| Cellulose 1,7/50 + 10% CMC | 2.93 | 3,6 | 7,2 | 12,2 | 16,4 |
| Cellulose, 5,2/40 formalized | 2,89 | 5,8 | 12,0 | 17,8 | 22,6 |
| Cellulose 1,7/50, + 10% CMC mixed fiber, formalized | 3,00 | 9,1 | 20,4 | 22,3 | 26,9 |

The experiments show that all values are greatly increased as compared with those known before, and in part, an increase of over 100% is shown. It is interesting that the formalized mixed fiber proposed also has greatly increased absorptive value over the non-formalized mixed fiber.

Having thus described our invention, we claim:

1. In a process for the production of a tampon or like hygienic article having high fluid suction and holding power for aqueous physiological fluids, in which a viscose spinning solution is produced from cellulose xantogenate by dissolving in aqueous caustic soda, aging said spinning solution, spinning aged solution in an acid spinning bath, and cleaning and drying the resultant fibers the improvement consisting of, adding to the spinning solution about 5 to 20% by weight, of sodium carboxymethyl cellulose, based on the cellulose contained in the solution, cleaning partly reticulated fibers obtained, in an acid solution, formalizing the fibers, regenerating the sodium salt and washing the fibers until neutral.

2. A method which comprises formalizing 100 parts of a mixed fiber of about 90% cellulose and 10% sodium carboxymethyl cellulose, in a bath consisting of 50% by weight of 37% concentrated hydrochloric acid and about 20% by weight formaldehyde solution, washing the fiber neutral with water, then placing the fiber into a 10% solution of sodium hydrogen carbonate, regenerating the sodium salt of the carboxymethyl cellulose, then washing the fibers neutral again, in water containing 0.5% polyethylene glycol.

3. The method which comprises carding the fiber prepared according to claim 2, forming the carded fibers to form strips 50 mm. wide, and winding and pressing the strips to form tampons.

* * * * *